United States Patent [19]

Webster et al.

[11] Patent Number: 5,068,472

[45] Date of Patent: * Nov. 26, 1991

[54] MULTISTEP SYNTHESIS OF HEXAFLUOROPROPYLENE

[75] Inventors: James L. Webster, Parkersburg, W. Va.; Swiatoslaw Trofimenko; Paul R. Resnick, both of Wilmington, Del.; Douglas W. Bruhnke, Landenberg; Jan J. Lerou, Chadds Ford, both of Pa.; William H. Manogue, Newark; Leo E. Manzer, Wilmington, both of Del.; Elrey L. McCann, Mendenhall, Pa.; Steven H. Swearingen, Wilmington; James A. Trainham, Newark, both of Del.; Cristobal Bonifaz, Conway, Mass.

[73] Assignee: E. I. Du Pont de Nemours and Company, Wilmington, Del.

[*] Notice: The portion of the term of this patent subsequent to Aug. 27, 2008 has been disclaimed.

[21] Appl. No.: 452,404

[22] Filed: Dec. 19, 1989

[51] Int. Cl.$^5$ .................... C07C 17/00; C07C 17/08
[52] U.S. Cl. .................... 570/157; 570/165; 570/166; 570/168; 570/169
[58] Field of Search ............... 570/155, 156, 157, 168, 570/161, 175, 176

[56] References Cited

U.S. PATENT DOCUMENTS

| 2,558,703 | 6/1951 | Gochenour . |
| 2,758,138 | 8/1956 | Nelson . |
| 2,873,630 | 3/1975 | West . |
| 2,900,423 | 8/1959 | Smith . |
| 2,970,176 | 1/1961 | Ten Eyck . |
| 3,258,500 | 6/1966 | Swamer et al. . |
| 3,306,940 | 2/1967 | Halliwell . |
| 3,436,430 | 4/1969 | Hall . |
| 3,459,818 | 8/1969 | Ukihashi . |
| 3,803,241 | 4/1974 | Stolkin et al. . |
| 3,865,885 | 2/1975 | Bruce . |

FOREIGN PATENT DOCUMENTS 1077932 8/1967 United Kingdom .

OTHER PUBLICATIONS

Sheppard & Shafts, Org. Fluor. Chem, 1969, pp. 74–81.
Hudlicky, Chem. of Org. Fluor. Compounds, 1962, pp. 481–489.

Primary Examiner—Alan Siegel
Attorney, Agent, or Firm—Donald W. Huntley

[57] ABSTRACT

The present invention relates to multistep syntheses of hexafluoropropylene from hexachloropropylene. In all these syntheses the first step is a fluorination of the starting material; later steps convert the initial products to $CF_3$—$CFCl$—$CF_3$, which is dehalogenated to the desired product.

6 Claims, 1 Drawing Sheet

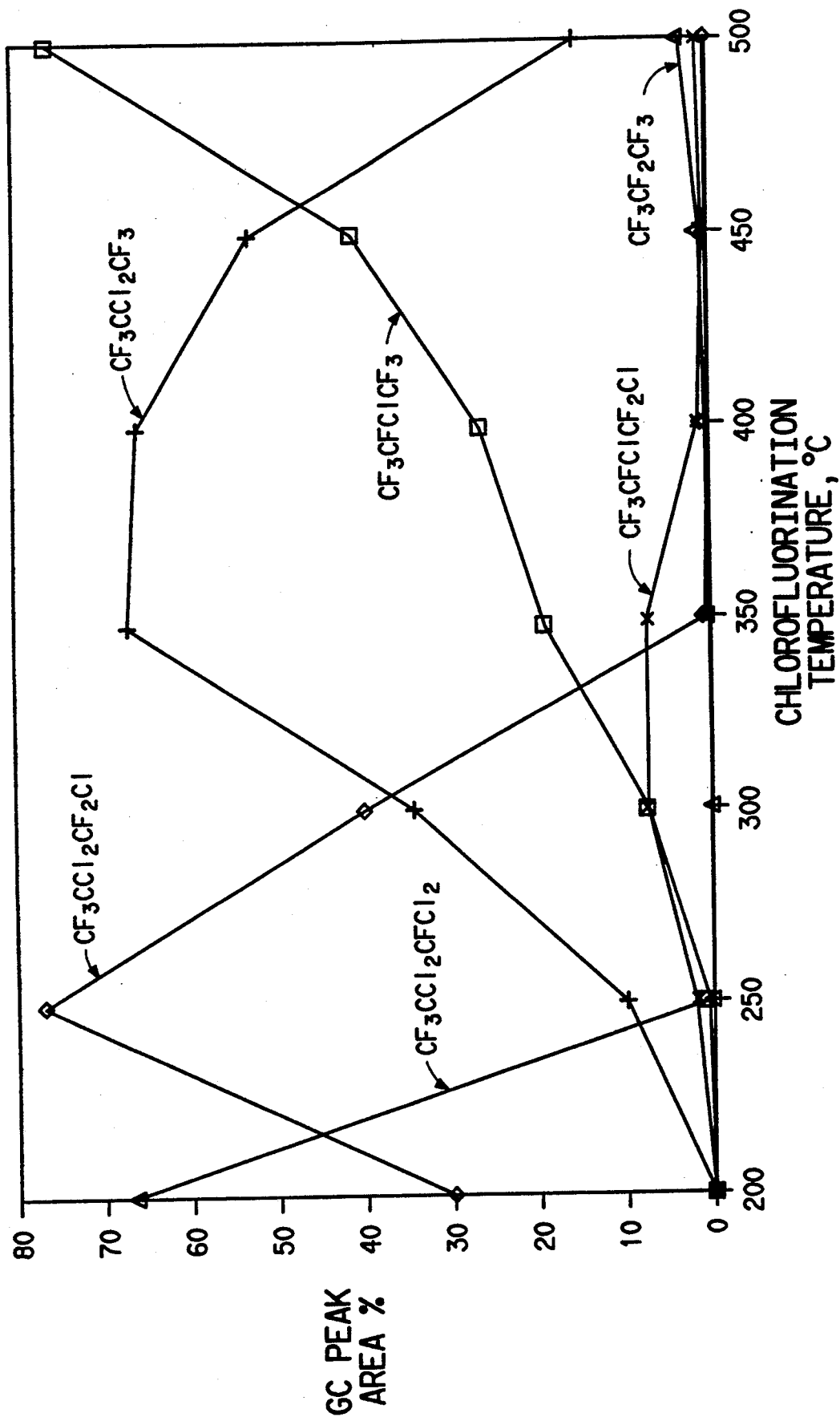

MULTISTEP SYNTHESIS OF HEXAFLUOROPROPYLENE

FIELD OF THE INVENTION

The present invention relates to multistep syntheses of hexafluoropropylene from hexachloropropylene.

BACKGROUND OF THE INVENTION

Hexafluoropropylene has been prepared by the pyrolysis of tetrafluoroethylene. This process has several disadvantages. Tetrafluoroethylene, which is itself difficult to prepare and purify, is an explosive compound, which must be stored and handled with the greatest care. The pyrolysis of tetrafluoroethylene inevitably makes some perfluoroisobutylene as a by-product, and this compound is extremely toxic and is costly to remove and destroy. Another preparative method for hexafluoropropylene is to make it simultaneously with tetrafluoroethylene by pyrolysis of $CHClF_2$. The product also contains the toxic by-product perfluoroisobutylene, and the process provides a particular mixture of the two products, which may be different from the ratio of products desired by the user. Both of the above synthetic methods are carried out at high temperatures, so it is necessary to make the equipment from rare and expensive metals. Patents describing these processes include U.S. Pat. No. 3,873,630, U.S. Pat. No. 2,970,176, U.S. Pat. No. 3,459,818, U.S. Pat. No. 2,758,138, and U.S. Pat. No. 3,306,940.

U.S. Pat. No. 2,558,703 discloses the Sb-catalyzed fluorination of $C_3Cl_6$ to $CF_3CCl=CCl_2$ at 77% yield, but does not mention further fluorination. U.S. Pat. No. 4,680,406 discloses the carbon-catalyzed reaction of $C_3Cl_6$ with HF to give, in addition to unreacted starting material and a by-product, $C_3F_5Cl_3$, $C_3F_4Cl_2$, and $C_3F_3Cl_3$. Conditions are limited to a small number of catalysts. U.S. Pat. No. 2,900,423 relates to the synthesis of hexafluoropropylene by hydrogenation of $CF_3$—$CFCl$—$CF_3$ over a catalyst. The patent gives no information about the washing step or the residual K in the catalyst. No information on catalyst life is presented, the longest run lasting only three hours.

The discovery of an improved process which provides chlorofluorocarbons in high yield in one step from the known $C_3Cl_6$ makes possible several reaction sequences for making hexafluoropropylene.

SUMMARY OF THE INVENTION

An object of the invention is to provide a process for the fluorination of hexachloropropylene to make perhalocarbon intermediates, followed by conversion to hexafluoropropylene. It permits selection of a sequence of steps in which I. the first step is selected from the class consisting of
 a) the vapor phase chlorofluorination of hexachloropropylene to make at least one perhalopropane;
 b) the liquid phase reaction of hexachloropropylene with HF in the presence of a catalyst selected from antimony pentahalide, antimony trihalide, and tantalum pentahalide to make at least one perhalopropane;
 c) the liquid phase reaction of hexachloropropylene with HF in the presence of a catalyst selected from antimony pentahalide and antimony trihalide to make at least one perhalopropylene, followed by further liquid phase reaction of the product with HF in the presence of antimony pentachloride to make at least one perhalopropane;
 d) the liquid phase reaction of hexachloropropylene with HF in the presence of tantalum pentahalide to make at least one of the class consisting of perhalopropylene and pentahalopropane, followed by the vapor phase chlorofluorination of the intermediate mixture to a more highly fluorinated perhalopropane;

II. the second step is the fluorination of the product of I (a), (b), (c), or (d) to make $CF_3$—$CFCl$—$CF_3$; and III. the third step is the dehalogenation of $CF_3$—$CFCl$—$CF_3$ to make hexafluoropropylene by a process selected from
 a) catalytic hydrogenation, and
 b) dehalogenation with Zn, Mg, Cu, Fe or Ni in a polar organic solvent at 25°–200° C.; and IV. the last step is isolation of hexafluoropropylene.

DETAILED DESCRIPTION

Definitions

For the purpose of this disclosure:

Metal catalyst means a solid metal-containing catalytic salt or oxide as charged to the reactor. In many of the reactions described, the catalyst may undergo unknown changes in composition during pretreatment and reaction steps. Metals which react with HF to give volatile compounds are not preferred.

Contact time means the volume of catalyst charged to the reactor in ml, divided by the sum of all gas flow rates, in ml/sec, as measured at standard temperature and pressure.

Halogen means Cl and F.

Chlorofluorination means reaction of a feed material with a mixture of $Cl_2$ and HF.

In the following sequences of reactions, conventional procedures may be used for reactant and product isolation and, if desired, recycle. Especially useful techniques are fractional distillation or partial condensation. It is possible not only to have a separate recovery system for each reaction, as is conventional, but in some cases it is possible to combine the product streams for product isolation.

Chlorine, HF and HCl are separated by conventional methods. Therefore, the lowest boiling material is hexafluoropropylene, which is the final product desired. Next lowest boiling among saturated perhalocarbon intermediates is $CF_3$—$CFCl$—$CF_3$, which is used in the last step of each sequence of this invention. Intermediates containing two or more chlorine atoms boil higher, and may be recycled with or without isolation.

Step I (a) is carried out in the presence of a catalyst comprising a solid metal-containing salt or metal oxide or consisting of purified Philippine based coconut charcoal at a temperature between 100° and 550° C. and a contact time between 0.01 and 300 seconds, using a chlorine:$C_3Cl_6$ molar ratio of 1–5, preferably 1.5–4, and an HF:$C_3Cl_6$ molar ratio of 3–60, preferably 20–50, and separating from the reaction product by conventional means one or more of the perhalopropanes A. $C_3F_3Cl_5$
B. $C_3F_4Cl_4$,
C. $C_3F_5Cl_3$,
D. $C_3F_6Cl_2$, and
E. $CF_3$—$CFCl$—$CF_3$ Step I (b) is carried out with agitation at 30° to 250° C., preferably 40° to 160° C., in excess HF, using at least 0.5 wt % catalyst.

Step I (c) is carried out with agitation at 0°-200° C., preferably 30°-60°, for 1-180 minutes with excess HF and at least 1 wt % catalyst, but preferably with excess catalyst.

Step I (d) is carried out with agitation at 30°-250° C., preferably 40°-160° C., using excess HF and any amount of $TaF_5$ for a time sufficient to convert all starting material.

Step II is carried out by a process selected from
a) vapor phase reaction with HF at 250°-465° C. in the presence of $CrCl_3$ catalyst; and
b) liquid phase fluorination with $SbCl_5$/HF or $SbF_3$ at 25°-250° C.

Step III (a) is hydrogenation over a catalyst of Co, Ni, or Cr optionally promoted with a compound of Mo, V., W., Hg, Fe, I or Be, which catalyst has been reduced with hydrogen, at a temperature of 250°-550° C. and a pressure between 0 and 100 atmospheres gauge for 0.1-120 seconds.

The process may also be conducted starting with perchloropropane, which dehalogenates to hexachloropropylene in the first step.

Underfluorinated intermediates in any given step may be recycled after isolation.

CHLOROFLUORINATION

The catalysts which are effective for the chlorofluorination of a feed containing hexachloro propylene include compounds of the metallic elements. In use they may be in the form of their fluorides, oxyfluorides, chlorides, oxychlorides or oxides, but as charged to the reactor they may be in the form of any compounds convertible to the above compounds under reaction conditions, such as pseudohalides and acid salts. They may be used either alone or in combination and in the presence or absence of a support such as, but not limited to, elemental carbon. Some minerals such as ceria and didymia contain mixtures of rare earths such as La, Sm, Nd, and Pr, and the salts of these minerals may be more practical to use than those of the pure elements.

When hydrous chromium oxide is used in making a catalyst, that catalyst is preferably heated to 450° C. for about one hour with a flow of a gaseous diluent such as nitrogen, to dehydrate the hydrous chromium oxide before the catalyst is used. This dehydration treatment makes chromium oxide. While various kinds of $Cr_2O_3$ may be used as catalyst in this invention, $Cr_2O_3$ is preferred.

Preferred catalysts for the synthesis of $CF_3$—$CCl_2$—$CF_3$ are purified Philippine coconut charcoal and Cr compounds supported on the same charcoal.

In the vapor phase catalytic chlorofluorination of hexachloropropylene, a temperature may be employed of between 100° C. and 550° C. However, the preferred temperature is 200° C. to 500° C. The most preferred temperature is 300° C. to 450° C. The temperature used depends on the contact time chosen, the catalyst used, and the time the catalyst has been on stream.

In the chlorofluorination of hexachloropropylene the mole ratio of chlorine to $C_3Cl_6$ may vary from 1:1 to 5:1, preferably 1.5:1 to 4:1. The concentration of hydrogen fluoride in relationship to $C_3Cl_6$ may vary over a fairly broad range. Illustratively, mole ratios of hydrogen fluoride to $C_3Cl_6$ may be from 3 to 60, with a preferred range of 20 to 50.

In practice, it is convenient to recycle halocarbons that are not fluorinated to the desired degree, so that they will be converted to desired products.

The reaction pressure is not critical. Preferably it may be between 1 and 40 atmospheres. About 20 atmospheres is preferred to allow easy separation of HCl from the halocarbons without requiring compression.

The yield of desired products will be determined to a large extent by the ratio of reactants and the temperature and contact time of the reactant materials with the catalyst. Contact times of the order of 300 seconds or less are suitable. Preferred contact times are 0.01 to 100 seconds. Most preferred contact times are 0.05 to 15 seconds.

General Procedure for Product Analysis

Product analysis was achieved by gas chromatography using a 3 m column from Supelco packed with 5% Krytox ® fluorinated oil supported on Carbopack ® B graphitized carbon black. Sample injection was accomplished by an on-line sample valve. The analysis was done at 70° C. for 8 minutes followed by temperature programming at 8 degrees per minute up to 200° C. and held at 200° C. for an additional 16 minutes. Product analyses are reported as relative area %.

Examples

In all of the Examples herein: Yield, as reported in the examples, is calculated from peak areas obtained in gas chromatographic analysis. This is a common technique in product identification, even though various compounds have somewhat different response factors.

Conversion of $C_3Cl_6$ in all chlorofluorination reactions is complete. Conversion to a particular product in the examples is calculated from peak areas obtained in gas chromatographic analysis.

Temperature in a tubular reactor of less than about 1 cm in diameter is measured with a thermocouple in the heat transfer medium outside the tube. Temperature in a tubular reactor of more than about 1 cm diameter is measured with a thermocouple in an internal well. In large scale reactors, there are several thermocouples in the well so that the temperature profile can be observed.

SYNTHESES OF HEXAFLUOROPROPYLENE

I. Sequence of Reactions Using Vapor Phase Chlorofluorination to Saturated Perhalopropanes a) Chlorofluorination of $C_3Cl_6$ to $CF_3$—$CCl_2$—$CF_3$, recycling all more lightly fluorinated intermediates.
b) $CF_3$—$CCl_2$—$CF_3$ + HF → $CF_3$—$CFCl$—$CF_3$
c) Dehalogenation of $CF_3$—$CFCl$—$CF_3$ to hexafluoropropylene

EXAMPLES OF SEQUENCE I

Ia) Chlorofluorination of $C_3Cl_6$ to $CF_3$—$CCl_2$—$CF_3$, recycling all more lightly fluorinated intermediates.

The continuous flow reactor was an Inconel tube with an outside diameter of 0.5 inch (1.27 cm) and a length of 12" (30.5 cm), heated by a Lindberg electrical furnace. It was charged with the desired amount of catalyst, and purged with nitrogen. The reactor temperature was increased via a heated fluidized sand bath to 450° C. The nitrogen flow was maintained through the reactor during the heating period. When a temperature of about 450° C. was achieved, the HF flow was initiated and the nitrogen flow was discontinued. The temperature was then adjusted to the desired value. The HF flow was decreased to the desired value followed by initiating the chlorine and C₃Cl₆ flows at the desired values.

The liquid feedstock was metered by a high pressure precision Gilson pump and totally raporized before entering the reactor. HF and chlorine were metered into the reactor by mass flow controllers.

The gas stream leaving the reactor was analyzed hourly by on-line gas chromatography using a 6 m column from Supelco packed with 5% Krytox ® oil supported on Carbopack B. Sample injection was accomplished by an on-line sample valve. The analysis was done at 70° C. for 8 minutes followed by temperature programming at 8 degrees per minute up to 200° C. and held at 200° C. for an additional 16 minutes. Product identification was by retention times with confirmation by off-line GC/MS analysis. Product analyses are reported as relative area %.

In preparing metal catalysts, the desired amount of metal chloride was dissolved in 35 to 75 ml of water and the entire solution poured over 40 cc of commercial charcoal granules (purified Philippine based coconut charcoal called PCB carbon, from Calsicat Division of Mallinckrodt, Inc.). The resulting mixture was allowed to stand at room temperature for one hour and was then placed in a vacuum oven at 110° C. for 16 to 24 hours to remove the water. The catalyst was then pretreated by heating in an atmosphere of nitrogen gas at 450° C. followed by heating in HF at 450° C. prior to its use as a chlorofluorination catalyst.

Five g (10 ml) of a 7.5 wt % CrCl₃ on PCB carbon were charged to the reactor described above. Several experiments were run using a contact time of 7.5 seconds, a chlorine:C₃Cl₆ mole ratio of 2:1, and an HF:C₃Cl₆ mole ratio of 30:1. The results are presented in the following table, in which 217 means C₃F₇Cl, 216 means C₃F₆Cl₂, 215 means C₃F₅Cl₃, C1 means one-carbon products, and C2 means two-carbon products.

|         | 217  | 216   | 215   | C1   | C2   |
|---------|------|-------|-------|------|------|
| 375° C. | 0.00 | 75.7  | 18.88 | 0.18 | 2.07 |
| 400° C. | 0.01 | 92.31 | 5.06  | 0.42 | 1.78 |
| 425° C. | 0.09 | 94.99 | 1.92  | 0.63 | 2.09 |
| 450° C. | 0.52 | 93.97 | 1.17  | 1.01 | 3.08 |

These data show that at 425° C., the conversion and yield to 216 are 95%, and since 215 is recyclable, the yield to 216 and recyclable by-product is 96.9%. At 400° C., the yield to 216 and recyclable by-product is 97.4%.

Ib) CF₃—CCl₂—CF₃+HF→CF₃—CFCl—CF₃

Example 59. CF₃—CCl₂—CF₃ (12 cc/min) and HF (48 cc/min) were passed over Cr₂O₃ at 465° C. and a contact time of 7.6 seconds. The conversion to the desired product decreased with time, as usually happens in catalytic reactions, but after 850 hours on stream, the product contained 70% starting material, 26% CF₃—CFCl—CF₃, 0.9% perfluoropropane, 0.1% C₃F₆HCl, and 0.1% CF₃—CCl=CF₂. Thus the yield to CF₃—CFCl—CF₃ from converted starting material was 87%.

Example 60. Similar results were obtained in shorter runs at 100-200 psig (690-1380 kPa) over the same kind of catalyst. For example, at 100 psig (690 kPa), 23 cc/min of CF₃—CCl₂—CF₃ and 53 cc/min HF were passed over Cr₂O₃ at a contact time of 24 seconds at 437° C. to give 32% conversion to CF₃—CFCl—CF₃ at high yield after 34 hours on stream.

Example 61. This step (Ib) reaction was also carried out at a pressure of 100 psig (690 kPa). The reaction was carried out in a U-tube with inside diameter 0.43 inches (1.1 cm), using 30 cc Cr₂O₃ catalyst at 400°-437° C. The flow of HF was 53 cc/minute and the flow of CF₃—CCl₂—CF₃ was 23 cc/minute. The contact time was 24 seconds. The results are presented below:

| Temp, °C. | Conversion to CF₃—CFCl—CF₃ | Yield, assuming other products were starting material |
|-----------|----------------------------|-------------------------------------------------------|
| 400       | 5.5%                       | 89%                                                   |
| 412       | 10                         | 83                                                    |
| 425       | 20                         | 88                                                    |
| 437       | 32                         | 86                                                    |

The halogen exchange reaction of step (Ib) was also carried out under completely different conditions, using SbF₅ reactant. In general, replacement of Cl with F can be carried out with Sb fluorides in the (III) or (V) valence state, or a mixture of these. Sb chlorides plus HF can also be used. The temperature range can be 25°-250° C., and the time can be 15 minutes to 15 hours. Preferably, the temperature is 150°-200° C., the reagent is SbF₅, and the time is long enough to provide a reasonable conversion of starting material. Higher temperature, longer time, and higher Sb valence tend to result in higher conversion. As pointed out in Sheppard and Sharts, Organic Fluorine Chemistry, W. A. Benjamin, Inc., 1969, the presence of F on a carbon adjacent to a C-Cl bond deactivates the Cl toward replacement using Sb halide. The group —CCl₃ is easier to fluorinate than the group —CCl₂—. Carbon-fluorine bonds activated by an adjacent double bond react more readily with Sb fluorides.

Example 62. 20.6 g SbF₅ and 20 g CF₃—CCl₂—CF₃ were charged to a 150 ml Hastelloy pressure tube and agitated for 4 hours at 200° C. The tube was cooled to room temperature and discharged into an Orsat bulb for analysis, which showed 70% CF₃—CFCl—CF₃ and 29% starting material. Thus the conversion was 70% and the yield from converted starting material was 98%.

Ic) Dehalogenation of CF₃—CFCl—CF₃ to hexafluoropropylene:

Ic (i) Hydrogenation. While any hydrogenation catalyst could be used, the most active catalysts, such as Pt and Pd, are poor selections because, in addition to the desired products, they lead to the addition of hydrogen across any double bond present or to the substitution of hydrogen for chlorine, thus reducing the yield of desired products and requiring recycle. These effects are not desirable, but do not substantially reduce the overall yield to hexafluoropropylene, because the hydrogen-containing by-products can be recycled to the chlorofluorination step. Catalysts containing excessive amounts of Ni may give this somewhat undesirable result.

Catalysts which are preferred include, as charged to the reactor, common hydrogenation catalysts such as Cu, Ni, Cr, or combinations thereof, optionally promoted with compounds of Mo, V, W, Ag, Fe, K, Ba, or combinations thereof. It is not critical whether the catalysts are supported or not, but some of the better catalysts include unsupported copper chromite. However, supports which are unreactive to halocarbons, HF, and oxygen at hydrogenation temperatures and up to 100° higher such as metal fluorides, alumina, and titania, may be used. Particularly useful are supports of fluorides of metals of Group II of the Mendeleeff periodic table, particularly Ca. A preferred catalyst is made of equimolar quantities of Cu, Ni, and $Cr_2O_3$ on $CaF_2$.

An especially preferred catalyst contains 1.0 mole CuO, 0.2–1 mole NiO, 1–1.2 moles $Cr_2O_3$ on 1.3–2.7 moles of $CaF_2$, promoted with 1–20 weight %, based on the total catalyst, of an alkali metal selected from K, Cs, and Rb, preferably K. When K is the promoter, the preferred amount is 2–15 weight % of the total catalyst, but the method of adding the K is not critical. For example, it may be added as a salt or base.

This catalyst is not only useful for the reaction $CF_3$—$CFCl$—$CF_3+H_2\rightarrow CF_3CF=CF_2$, but also for corresponding hydrodehalogenations

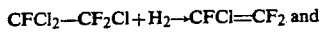

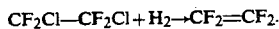

The catalyst is prepared by coprecipitating, from an aqueous medium, salts of copper, nickel and chromium with and preferably on calcium fluoride; washing, heating, filtering and drying the precipitate; followed by depositing an alkali metal salt on the precipitate; and calcining the precipitate to convert the copper, nickel and chromium to the respective oxides. Copper, nickel and chromium salts suitable for use herein include the chlorides, fluorides and nitrates, with the nitrates being especially preferred.

The catalyst may be granulated, pressed into pellets, or shaped into other desirable forms. The catalyst may contain a binder to help ensure the physical integrity of the catalyst during granulating or shaping the catalyst into the desired form. Suitable binders include carbon and graphite, with carbon being preferred. When a binder is added to the catalyst, it normally comprises about 0.1 to 5 weight percent of the weight of the catalyst.

Another group of catalysts which showed good lifetime in the hydrodehalogenation of $CF_3$—$CFCl$—$CF_3$, $CF_2Cl$—$CF_2Cl$, or $CFCl_2$—$CF_2Cl$ is 1.0 CuO/0.2–1 NiO/1–2 $Cr_2O_3$/0.4–1 $MoO_3$/0.8–4 $CaF_2$, optionally promoted with at least one compound from the group consisting of $MgF_2$, $MnF_2$, and $BaF_2$ or with a trace of Pd or $WO_3$. Two of these hydrodehalogenation runs were shut down after 153 and 361 hours, respectively, while still giving good results.

After it is charged to the reactor, the hydrogenation catalyst is reduced with hydrogen at or somewhat above the desired reaction temperature before the chlorofluorocarbon feed is started.

After use in the hydrogenation reaction for a period of time, the activity of the catalyst may decrease. When this occurs, the catalyst activity can be regenerated by stopping the flow of halocarbon, flushing the bed with a gas such as hydrogen, air, or oxygen, at a temperature near or up to 100° higher than the hydrogenation temperature for at least several minutes. (A temperature higher than the hydrogenation temperature is normally used, but a lower temperature can be used with hydrogen.) After the flushing step, the reactor temperature is readjusted to the hydrogenation temperature before resuming the hydrogenation reaction. While the inventors do not wish to be bound by any hypothesis, it is believed possible that catalyst activity deteriorates when the halocarbon feed deposits a small amount of polymer on the catalyst. Heating to a higher temperature in the presence of a flowing gas may pyrolyze the polymer to volatile fragments, which are swept away by the gas. The nature of the gas is not critical, but hydrogen is preferred.

A suitable temperature for the hydrogenation step is 250°–550° C., preferably 350°–475°, and most preferably 400°–450°. A suitable contact time is 0.1–120 seconds. A preferred contact time is 0.3–60 seconds, and the most preferred contact time is 0.5–15 seconds.

Suitable pressure in step (b) is 0–100 atmospheres gauge. Preferred is 0–50 atmospheres, and most preferred is 2–30 atmospheres.

As those skilled in the art appreciate, there is a relationship between catalyst activity, temperature, pressure, and contact time such that more active catalyst and higher pressure permit operation at lower temperature and shorter contact time. Ib.

(ii) Dehalogenation with a metal. The elements of $Cl_2$ or ClF can be removed from a halocarbon using a metal such as Zn, Mg, Cu, Fe, or Ni or a combination of such metals. It is preferable to use Zn. It is also preferable to use a polar organic solvent for this reaction, such as an alcohol, ether, dioxane, anhydride, or nitrile. The temperature may be 25°–200° C., preferably 70°–200° C., and the time of reaction, which depends on the reagent and the temperature, can be determined by routine experimentation. Examples of Step Ic) Dehalogenation of $CF_3$—$CFCl$—$CF_3$.

Ic (i) Hydrogenation.

Example 42. A 1:1 molar mixture of hydrogen and $CF_3$—$CFCl$—$CF_3$ was passed over a $BaCrO_4$-modified copper chromite catalyst at 400° C. and atmospheric pressure at a contact time of 15–20 seconds. In several experiments, the once-through conversion to hexafluoropropylene was 60–70%, with $C_3F_7H$ the major by-product. This could be recycled to step (a) for further chlorination, so the overall yield was estimated to be excellent.

Examples 43–45. For these examples, an Inconel 600 U-tube reactor was made from 24 inches (61 cm) of 0.5 inch (1.3 cm) tubing. Each arm of the U-tube was 8 inches (20.3 cm) long, as was the bottom. The inlet and outlet to the reactor were ¼ inch (0.64 cm) tubing, and tees allowed ⅛ inch (0.32 cm) thermowells to be placed in each end of the tube. The reactor tube was totally filled with catalyst so that as the cool feed gases were heated, they were in contact with the catalyst. The inlet thermowell indicated that the gases were at reaction temperature within the first 4 inches (10.2 cm) of the reactor length. Because of the preheat length and the length of tubing above the level of the alundum, the actual heated length of the reactor was assumed to be 12 inches (30.5 cm). A separate thermocouple was kept in the fluidized bath to verify the batch temperature.

The cooled product from the reactor was passed into a small polypropylene trap, then into a 20% KOH scrubber made of polypropylene. The heat of reaction of HF and HCl with the alkali was never great enough to heat the solution above 50° C. The product then went through a water scrubber, a small bed of Drierite ®, and then to a cold trap in dry ice/acetone where the products and unconverted reactants were collected.

The main analysis tool used for this work was a temperature programmable Hewlett-Packard 5880A gas chromatograph with a thermal conductivity detector.

This dual column unit was equipped with a pair of 8-foot×⅛ inch (2.43 m×0.32 cm) stainless steel columns packed with 1% SP-1000 on 60/80 mesh Carbopack B purchased from Supelco, Inc (catalog no. 1-2548). These columns were run With helium flows of 30 cc/minute. The column was started at 50° C. for three minutes, then heated to 150° C. at a rate of 20° C./minute, and held there for another 15 minutes if necessary.

Three methods were employed in preparing the various catalysts:

A. Pyrolysis of nitrates. In this method the ingredients such as commercial copper chromite, chromium nitrate, $MoO_3$, etc., were prepyrolyzed in a resin kettle until all the removable water and volatiles were gone, and then the residue was calcined at 650° C. for at least three hours, usually overnight.

B. The various metal cations were precipitated from aqueous solution by adding KOH and KF solutions. The crude solids were filtered, washed well with water, prepyrolyzed and calcined as above.

B*. This method was similar to B, except that precipitation was sequential, rather than simultaneous. Typically, $CaF_2$ was precipitated first, allowed to age at least 24 hours, and only then were the hydrated oxides of transition metals precipitated onto the $CaF_2$ particles.

Several dozen catalysts were evaluated, and most of them gave 80-97% yield from $CF_3—CFCl—CF_3$ to hexafluoropropylene. Three of the best runs are shown as Examples 43-45.

The catalyst for Example 43 was $CuO/Cr_2O_3/NiO/0.9 MoO_3/2.1 CaF_2$, made by method B.

Example 44 used a $CuO/NiO/Cr_2O_3/2.7CaF_2$ catalyst, prepared by method B*, and performed for over 130 hours of intermittent hydrogenation, and was still active as the experiment was voluntarily terminated.

Example 45 used as catalyst $CuO/1.2 Cr_2O_3/0.9 NiO/1.7 CaF_2$, prepared by method A.

The results for these examples are shown in Table VI.

Any by-products made in the hydrogenation step are recycled to step (a), so they do not represent a yield loss.

Example 46. This hydrogenation was also carried out at elevated pressure, as shown in this Example. A reactor was made of Inconel tubing with inside diameter 0.19 inches (0.48 cm). The reactor was charged with 1.0 g of $CuO/NiO/Cr_2O_3/2.7 CaF_2$, which was conditioned with hydrogen at atmospheric pressure at 550° C. for one hour. Then the reactor was pressurized with nitrogen and fed 95% pure $CF_3—CFCl—CF_3$ and hydrogen at 150-200 psig (1034-1379 kPa) continuously at 420° C. for 46 hours. The conversion of $CF_3—CFCl—CF_3$ was 20%, and the yield of hexafluoropropylene from converted $CF_3—CFCl—CF_3$ was 98-100%.

For comparison, a similar run was made under similar conditions with the $Cu/Ni/Cr_2O_3$ catalyst of U.S. Pat. No. 2,900,423, which gave higher yield to hexafluoropropylene for the first 10 hours, after which the yield decreased sharply while the yield in Example 46 was steady or increased.

Example 45A used pellets of a $CuO/NiO/Cr_2O_3/2.7 CaF_3$ catalyst which had been soaked in KOH until they contained, after drying, 7.9 weight percent K. The yield to HFP at 400° C. or at 420° C. after extended operation was quite superior to that obtained with similar catalysts containing 0.08% or 0.1.2% K, and was slightly superior to that obtained with similar catalysts containing 4.6, 8.9, 9.6, and 15.1% K.

Ic (ii). Reaction with a suitable reducing metal.

Example 47. Into a one-liter autoclave containing a few steel bearings to facilitate agitation were placed 65 g. zinc dust, 15 g. copper powder, and 250 ml. acetonitrile. The autoclave was cooled and charged with 100 g. of halocarbons, of which 96.3 g. was $CF_3—CFCl—CF_3$, 0.7 g. was hexafluoropropylene, and 1.2 g. was $C_3F_7H$. The autoclave was shaken for 8 hours at 150° C. After cooling to room temperature, the contents were vented slowly into a cylinder cooled to −80° C. Gas chromatographic analysis of the product showed 55% of the $CF_3—CFCl—CF_3$ was converted. The yield to hexafluoropropylene was 29% and the yield to $C_3F_7H$ was 68%. This by-product can be chlorinated to $CF_3—CFCl—CF_3$ for recycle.

II. Sequence of Reactions Using Liquid Phase Chlorofluorination to Saturated Perhalopropanes a) Liquid phase chlorofluorination of $C_3Cl_6$ to perhalopropanes.
b) Perhalopropanes $+HF \rightarrow CF_3—CFCl—CF_3$
c) Dehalogenation of $CF_3—CFCl—CF_3$ to hexafluoropropylene

EXAMPLES OF SEQUENCE II

IIA) Liquid phase chlorofluorination of $C_3Cl_6$ to perhalopropanes.

Example a) A shaker tube was charged with 74.7 g hexachloropropylene, 6.0 g antimony pentachloride, 50 g anhydrous HF, and 22 g chlorine. After heating and shaking for one hour at 40° C., two hours at 200° C., and four hours at 250° C., the contents were added to a water/ice mixture. The lower layer, 61.9 g, showed on analysis that the experiment gave a 30% yield to $CF_2Cl—CCl_2—CF_3$ and a 50% yield to $CFCl_2—CCl_2—CF_3$.

Example b) A shaker tube was charged with 74.7 g $C_3Cl_6$, 4.5 g tantalum pentafluoride, 50 g anhydrous HF, and 25 g chlorine. After heating and shaking for two hours at 40° C., two hours at 200° C., and two hours at 250° C., the contents were added to a water/ice mixture. The lower layer, 60.6 g, analyzed for a 50% yield to $CF_2Cl—CCl_2—CF_3$ and a 28% yield to $CFCl_2—CCl_2—CF_3$.

Example c) A rocker bomb was charged with 373.5 g hexachloropropylene, 15.0 g antimony pentachloride, 180 g anhydrous HF, and 114 g chlorine. After heating and rocking at 40° C. for two hours and then 200° for six hours, the contents were added to an ice/water mixture. Distillation of the semisolid lower layer gave 303.0 g (79.5% yield) of $CFCl_2—CCl_2—CF_3$, b.p. 110°-112° C.

Example d) Hexachloropropylene (0.30 moles), HF (2.5 moles), antimony pentachloride (0.02 moles), and chlorine (0.30 moles) Were agitated and heated in a pressure vessel at 40° C. for one hour, then 200° for two hours, then 250° for 4 hours. The product was discharged into a water/ice mixture and analysis of the crude product showed a 61% yield to $CFCl_2—CCl_2—CF_3$, a 35% yield to $CF_2Cl—CCl_2—CF_3$, and 1% to $CF_3—CCl_2—CF_3$.

Example e) Hexachloropropylene (0.30 moles), HF (2.5 moles), antimony pentachloride (0.02 moles), and chlorine (0.35 moles) were agitated and heated in a pressure vessel at 40° C. for one hour, then 200° for four hours. The product was discharged into a water/ice mixture, giving an 82% yield to $CFCl_2—CCl_2—CF_3$ and a 15% yield to $CCl_3—CCl_2—CF_3$.

IIb. Perhalopropanes+HF→$CF_3$—CFCl—$CF_3$ (See Sequence Ib).

IIc. Dehalogenation of $CF_3$—CFCl—$CF_3$ to hexafluoropropylene (See Sequence Ic).

III. Sequence of Reactions Using Liquid Phase Chlorofluorination to $CF_3$—CCl=$CCl_2$ a) Chlorofluorination of $C_3Cl_6$ to $CF_3$—CCl=$CCl_2$
b) Chlorofluorination of $CF_3$—CCl=$CCl_2$ to $CF_3$—CFCl—$CF_3$
c) Dehalogenation of $CF_3$—CFCl—$CF_3$ to hexafluoropropylene

EXAMPLES OF SEQUENCE III

IIIa) Chlorofluorination of $C_3Cl_6$ to $CF_3$—CCl=$CCl_2$

A shaker tube was charged with 174.3 g of hexachloropropylene, 6.0 g of antimony pentachloride, and 50 g of anhydrous HF. After heating and shaking at 40° C. for three hours the contents were added to an ice-/water mixture. The lower layer was separated and distilled to give 128.1 g (91.7% yield) of $CF_3$—CCl=$CCl_2$, b.p. 85°.

IIIb) Chlorofluorination of $CF_3$—CCl=$CCl_2$ to $CF_3$—CFCl—$CF_3$

This step can be carried out using chromium oxide catalyst at a contact time of 16 seconds, using a temperature of 300°-500° C., as shown in FIG. 1. With this catalyst and contact time, temperatures in the range of 300°-400° give some of the desired product, but they also give large quantities of under-fluorinated products, which have to be recycled. At 400°, only $CF_3$—$CCl_2$—$CF_3$ has to be recycled. At 450°, a higher conversion to the desired intermediate is obtained. At 500°, $CF_3$—CFCl—$CF_3$ is the predominant product, but some perfluoropropane is formed and represents a yield loss unless there is a use for the saturated by-product.

A similar approach can be used with other catalysts and other contact times to select the best temperature for a given chlorofluorination reaction. Other catalysts that are very suitable for this reaction are chromium oxide on alumina, nickel chloride on alumina, and $Cr_{.5}Mn_{.5}O_2$.

An alternate way to proceed from $CF_3$—CCl=$CCl_2$ to $CF_3$—CFCl—$CF_3$ is to chlorofluorinate $CF_3$—CCl=$CCl_2$ in the liquid phase to make a perhalopropane.

Example f). A shaker tube was charged with 60.0 g of $CF_3$—CCl=$CCl_2$, 6.0 g antimony pentachloride, 20 g anhydrous HF, and 25 g chlorine. After heating and shaking for one hour at 40° C. and four hours at 200°, the contents were added to an ice/water mixture. The lower layer was separated and distilled to give 37.7 g (52.9% yield) of $CF_2Cl$—$CCl_2$—$CF_3$, b.p. 70°.

This intermediate can be chlorofluorinated in the vapor phase to make $CF_3$—CFCl—$CF_3$ as in Sequence Ib.

IIIc) Dehalogenation of $CF_3$—CFCl—$CF_3$ to hexafluoropropylene (See Sequence Ic).

IV. Sequence of Reactions Using Liquid Phase Fluorination of $C_3Cl_6$ to a Mixture of Pentahalopropanes and Optionally $CF_3$—CCl=$CCl_2$ a) Liquid phase fluorination of $C_3Cl_6$ to a mixture of pentahalopropanes and optionally $CF_3$—CCl=$CCl_2$
b) Chlorofluorination of the products of (a) to $CF_3$—CFCl—$CF_3$
c) Dehalogenation of $CF_3$—CFCl—$CF_3$ to hexafluoropropylene

EXAMPLES OF SEQUENCE IV

IVa) Liquid phase fluorination of $C_3Cl_6$ to a mixture of pentahalopropanes and optionally $CF_3$—CCl=$CCl_2$ Example g) A shaker tube was charged with 74.7 g $C_3Cl_6$, 5.5 g tantalum pentafluoride and 50 g anhydrous HF. After heating and shaking for one hour at 40° C. and four hours at 200° C., the contents were added to an ice/water mixture. The lower layer, 45.5 g, was shown by infrared spectroscopy to be a mixture of $CF_2Cl$—CHCl—$CF_3$ (20%), $CF_3$—CCl=$CCl_2$ (37%), and $CFCl_2$—CHCl—$CF_3$ (16%).

Example h) A shaker tube was charged with 75.7 g $C_3Cl_6$, 4.5 g tantalum pentafluoride, and 50 g anhydrous HF. After heating and shaking for two hours at 40° C., two hours at 200°, and two hours at 250°, the contents were added to an ice/water mixture. The lower layer, 24.5 g, was shown by infrared spectroscopy to be a mixture of $CF_3$—CHCl—$CF_3$ (10% yield) and $CF_2Cl$—CHCl—$CF_3$ (29% yield).

Example i) A shaker tube was charged with 74.7 g $C_3Cl_6$, 5.5 g tantalum pentafluoride and 30 g anhydrous HF. After heating and shaking for five hours at 120° C. the contents were added to an ice/water mixture. The lower layer, 59 g, contained $CF_2Cl$—CHCl—$CF_3$ (8% yield), $CF_3$—CCl=$CCl_2$ (37% yield), and $CFCl_2$—CHCl—$CF_3$ (46% yield).

IVb) Chlorofluorination of the products of (a) to $CF_3$—CFCl—$CF_3$

This step can be carried out in the vapor phase as in Sequence III(b)

IV(c) Dehalogenation of $CF_3$—CFCl—$CF_3$ to hexafluoropropylene (See Sequence Ic).

We claim:

1. A process for the preparation of hexafluoropropylene comprising, under effective reaction conditions:
   (a) fluorinating or chlorofluorinating $CCl_3CCl$=$CCl_2$, in the presence of a catalyst and by contacting the $CCl_3CCl$=$CCl_2$ with chlorine and hydrogen fluoride to produce perhalogenated C-3 chlorofluorocarbons;
   (b) hydrofluorinating any unsaturated chlorofluorocarbons of step (a) by contacting with excess HF in the presence of metal-containing catalyst to saturated perhalogenated chlorofluorocarbons;
   (c) fluorinating the saturated perhalogenated chlorofluorocarbons resulting from steps (a) and (b) by contacting with HF in the presence of metal-containing catalyst to produce $CF_3CFClCF_3$; and
   (d) hydrodehalogenating said $CF_3CFClCF_3$ to hexafluoropropylene by contacting with hydrogen in the presence of a potassium-containing catalyst.

2. The process of claim 1 wherein step (a) is carried out in the vapor phase.

3. The process of claim 1 or 2 wherein there is substantially no perfluoroisobutylene produced as a by-product.

4. A process of claim 1 wherein the catalyst in step (a) is a metal-containing catalyst.

5. A process of claim 1 wherein the mole ratio of chlorine to $CCl_3CCl$=$CCl_2$ in step (a) is about from 1:1 to 5:1.

6. A process of claim 5 wherein the mole ratio of chlorine to $CCl_3CCl$=$CCl_2$ in step (a) is about from 1.5:1 to 4:1.

* * * * *